(12) United States Patent
Bergersen

(10) Patent No.: US 7,861,721 B2
(45) Date of Patent: Jan. 4, 2011

(54) APPLIANCE, SYSTEM AND METHOD FOR PREVENTING SNORING

(75) Inventor: Earl O. Bergersen, Dorado, PR (US)

(73) Assignee: Ortho-Tain Inc, Winnetka, IL (US)

( * ) Notice: Subject to any disclaimer, the term of this patent is extended or adjusted under 35 U.S.C. 154(b) by 255 days.

(21) Appl. No.: 12/077,394

(22) Filed: Mar. 19, 2008

(65) Prior Publication Data

US 2008/0236597 A1    Oct. 2, 2008

Related U.S. Application Data

(60) Provisional application No. 60/920,732, filed on Mar. 28, 2007.

(51) Int. Cl.
*A61F 5/56* (2006.01)
*A61C 7/00* (2006.01)

(52) U.S. Cl. .......................... 128/848; 433/6

(58) Field of Classification Search .............. 128/846, 128/848, 858, 859, 861–863; 433/6, 25, 433/2, 140; 482/10, 11
See application file for complete search history.

(56) References Cited

U.S. PATENT DOCUMENTS

| | | | |
|---|---|---|---|
| 5,601,093 A * | 2/1997 | Sheehan | 128/848 |
| 5,876,199 A | 3/1999 | Bergersen | |
| 6,129,084 A * | 10/2000 | Bergersen | 128/848 |
| 6,299,581 B1 * | 10/2001 | Rapoport et al. | 600/484 |
| 7,476,180 B1 * | 1/2009 | Cobb | 482/11 |
| 2005/0089822 A1 * | 4/2005 | Geng | 433/215 |
| 2009/0098508 A1 * | 4/2009 | Baldwin | 433/140 |

FOREIGN PATENT DOCUMENTS

WO    WO 2008/121244    10/2008

OTHER PUBLICATIONS

PCT Written Opinion, Jul. 25, 2008, Ortho-Tain, Inc.
PCT Search Report, Jul. 25, 2008, Ortho-Tain, Inc.

* cited by examiner

*Primary Examiner*—Patricia M Bianco
*Assistant Examiner*—Tarla R Patel
(74) *Attorney, Agent, or Firm*—Patents + TMS, P.C.

(57) ABSTRACT

An appliance, a system and a method prevent snoring of a patient. The appliance opens an airway of the patient by advancing a lower jaw of the patient. A slot is formed on an upper shell and/or a lower shell of the appliance to receive teeth of the patient for wearing the appliance. A hinge connects the upper shell to the lower shell and resists the closing of the mouth of the patient to maintain the open airway of the patient. Wedges protrude from the hinge between the upper shell and the lower shell to further resist the closing of the mouth of the patient. Stiffer material of the hinge and/or the wedges relative to material of the upper shell and the lower shell requires more force to close the mouth of the patient and maintains the open airway of the patient during sleep. Extended margins may receive liner material to secure the appliance to the dentition. Lingual extensions on the lower arch help to maintain the lower jaw in a forward position relative to the upper jaw.

25 Claims, 2 Drawing Sheets

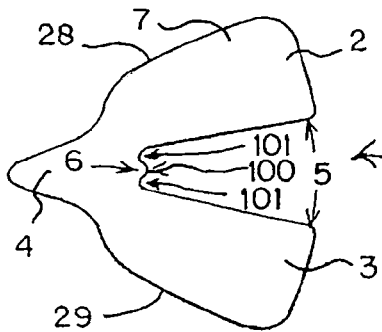
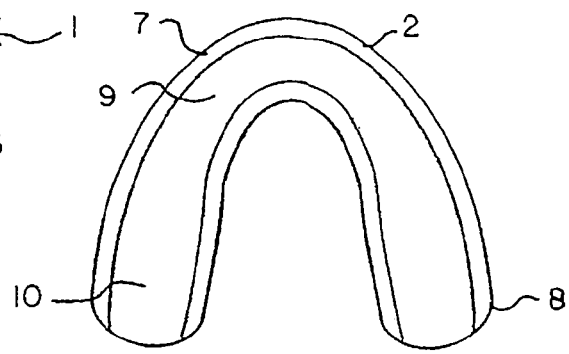
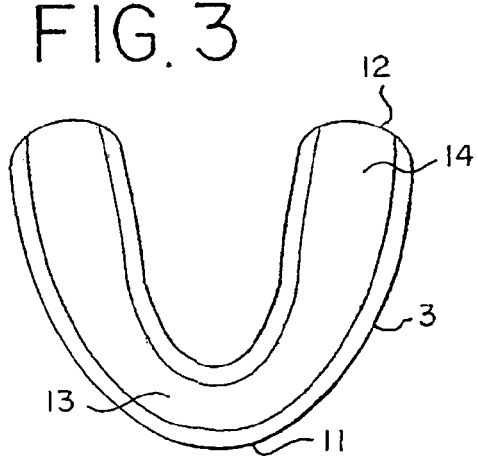
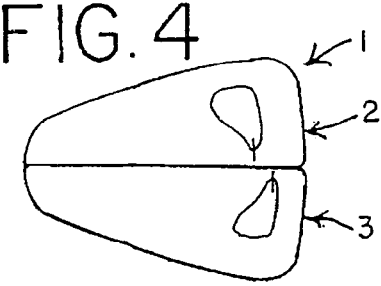
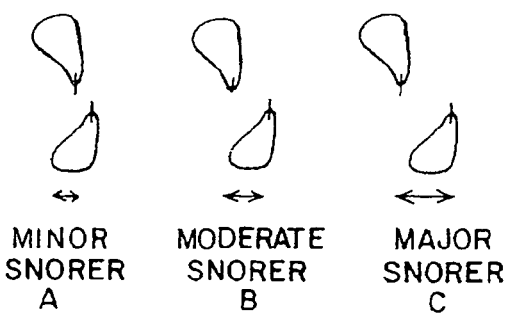
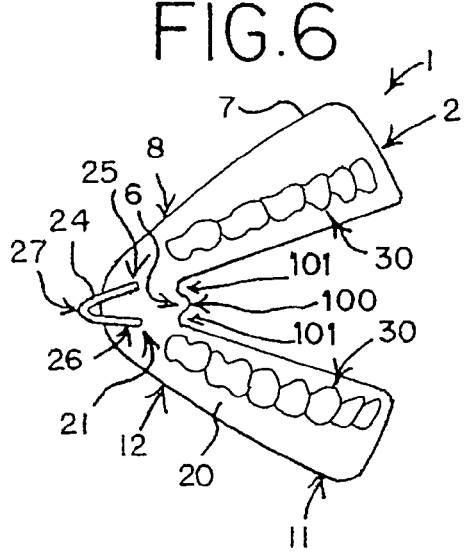

APPLIANCE, SYSTEM AND METHOD FOR PREVENTING SNORING

This application claims the benefit of U.S. Provisional Application Ser. No. 60/920,732, filed Mar. 28, 2007.

BACKGROUND OF THE INVENTION

The present invention generally relates to an appliance, a system and a method for preventing snoring. More specifically, the present invention relates to an appliance, a system and a method for opening an airway of a patient. Further, the appliance, the system and the method may open the airway of the patient by advancing a lower jaw of the patient. The appliance may be preformed, may be customized for the patient and/or may be both preformed and customized for the patient. The appliance may attach to teeth of the patient.

Snoring is caused by vibration of a soft palette tissue extension. If the lower jaw relaxes rearward in the mouth during sleep, the airway of the patient is narrowed. For example, narrowing of the airway often occurs due to sleeping on the back, relaxing of muscle and/or thickening of the neck area in overweight individuals. A narrowed airway causes the soft palette tissue extension to vibrate during inhalation that results in a snoring noise. A condition known as sleep apnea is associated with snoring. If the patient does not inhale enough air, a lack of oxygen causes the patient to labor for breath that interrupts sleep of the patient. As a result, the patient is tired and has difficulty remaining awake during the day.

It is generally known that a care provider, such as, for example, a dentist or an orthodontist examines the teeth and/or a mouth of the patient to determine abnormal oral functions of the patient. The care provider may provide an orthodontic appliance to be worn by a patient for correcting, for reducing and/or for minimizing the snoring of the patient. Traditionally, snoring is treated by opening the airway of the patient. Other methods involve opening nasal apertures to discourage breathing through the mouth; preventing sleeping on a back of the patient by placing a ball on a back of a neck of the patient; spraying a throat of the patient to aid in opening the airway; and attaching a small suction cup to a tip of a tongue of the patient to pull the tongue in a direction forward. Lack of comfort of the patient in these treatments hinders the success of the treatment. Often, the patient is less likely to diligently follow the treatment if discomfort and/or inconvenience exists.

A need, therefore, exists for an appliance, a system and a method for correcting snoring. Additionally, a need exists for an appliance, a system and a method for preventing snoring that may correct, may treat, may reduce and/or may minimize snoring by a patient. Further, a need exists for an appliance, a system and a method for preventing snoring that may be manufactured in a preformed version or in a custom-made version to be worn in the mouth of a patient. Still further, a need exists for an appliance, a system and a method for preventing snoring that provides a hinge between an upper and a lower shell that maintains an open position of the mouth of the patient. Moreover, a need exists for an appliance, a system and a method for preventing snoring that provides hinges or a connector in the rear of the dental appliance to maintain the position of the lower jaw relative to the upper jaw.

SUMMARY OF THE INVENTION

The present invention generally relates to an appliance, a system and a method for preventing snoring. More specifically, the present invention relates to an appliance, a system and a method for opening an airway of a patient. Further, the appliance, the system and the method may open the airway of the patient by advancing a lower jaw of the patient. The orthodontic appliance may be a preformed appliance and/or a custom-made appliance which may attach to the teeth of the patient.

The appliance may have a hinge between an upper and a lower shell that maintains an open position of the mouth of the patient. The appliance may have wedges in the rear of the dental appliance to maintain a position of the lower jaw relative to the upper jaw. The appliance may be preformed or may be custom-made to fit the mouth and/or to fit the dentition of the patient. The orthodontic appliance may be manufactured in a one-size-fits-all version or in various sizes. In the one-size-fits-all version, the orthodontic appliance may have a slot without sockets for receiving one or more teeth of the patient.

It is, therefore, an advantage of the present invention to provide an appliance, a system and a method for preventing snoring.

Another advantage of the present invention is to provide an appliance, a system and a method for preventing snoring which may provide a custom-made orthodontic appliance that treats a specific degree of severity of snoring of the patient.

A further advantage of the present invention is to provide an appliance, a system and a method for preventing snoring that may properly position jaws of a patient during sleep by the patient.

A still further advantage of the present invention is to provide an appliance, a system and a method for preventing snoring that may encourage a patient to breathe more readily through the mouth.

And, another advantage of the present invention is to provide an appliance, a system and a method for preventing snoring that may provide a hinge that fixes a position of a lower jaw of a patient with respect to an upper jaw of the patient.

Yet another advantage of the present invention is to provide an appliance, a system and a method for preventing snoring that may provide a wedge between an upper shell and a lower shell to maintain an open position of the appliance and as a result increase intake of air by the patient.

Yet another advantage of the present invention is to provide an appliance, a system and a method for preventing snoring that may provide extended margins to accept a liner material to retain the appliance to a dentition.

Moreover, another advantage of the present invention is to provide an appliance, a system and a method for preventing snoring that may provide upward extensions to the upper labial margin and downward extensions to the lower labial margin to more securely keep the appliance from slipping backward when the mouth opens.

Additional features and advantages of the present invention are described in, and will be apparent from, the detailed description of the presently preferred embodiments and from the drawings.

BRIEF DESCRIPTION OF THE DRAWINGS

FIG. 1 illustrates a side view of an appliance in an open position in an embodiment of the present invention.

FIG. 2 illustrates an upper view of an upper shell of an appliance in an embodiment of the present invention.

FIG. 3 illustrates a lower view of a lower shell of an appliance in an embodiment of the present invention.

FIG. 4 illustrates a side view of an appliance in a closed position in an embodiment of the present invention.

FIG. 5 illustrates positioning of teeth in various degrees of snoring severity.

FIG. 6 illustrates a side view of an appliance in an open position in an embodiment of the present invention.

DETAILED DESCRIPTION OF THE PRESENTLY PREFERRED EMBODIMENTS

Figure 7:
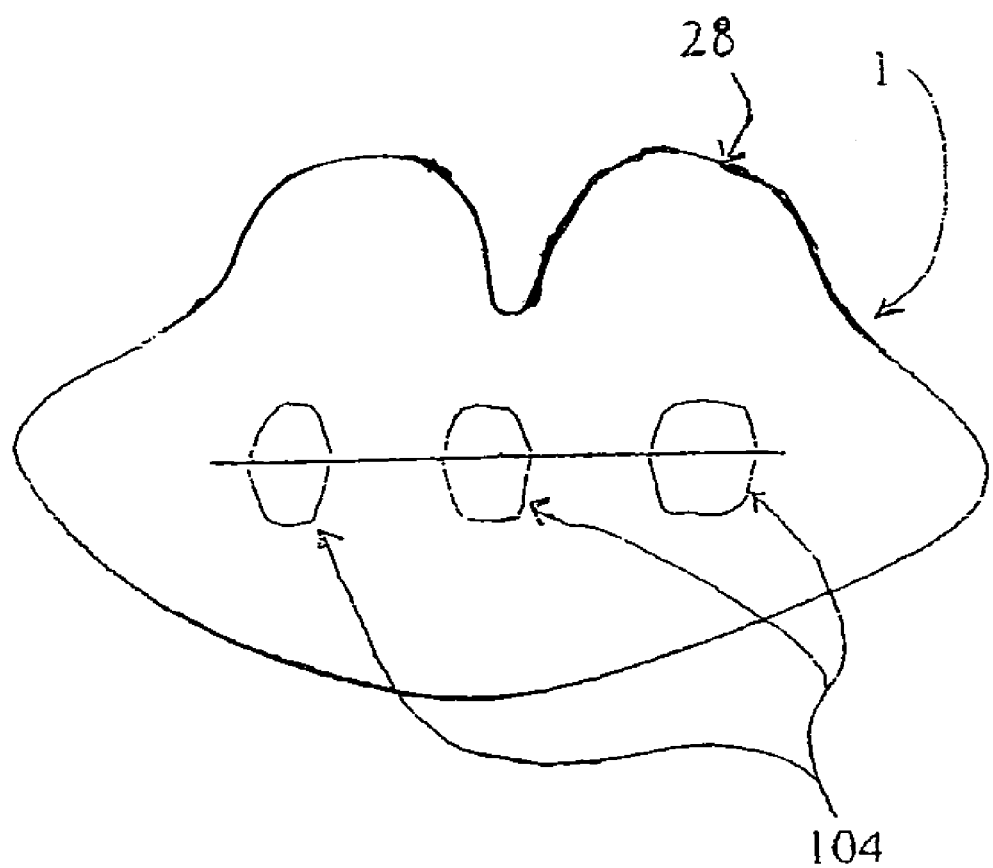
FIG. 7 illustrates a front view of an appliance in a closed position in an embodiment of the present invention.

The present invention generally relates to an appliance, a system and a method for preventing snoring. More specifically, the present invention relates to an appliance, a system and a method for opening an airway of a patient. The appliance, the system and the method may open the airway of the patient by advancing a lower jaw of the patient. The appliance may encourage the patient to breathe more efficiently through an oral cavity of the patient. An upper shell and a lower shell may attach to upper teeth and to lower teeth, respectively. A hinge connecting the upper shell and the lower shell may fix a position of the lower jaw relative to the upper jaw. The hinge may provide resistance against closing of the mouth by the patient. A wedge may protrude from the hinge between the upper shell and the lower shell to further resist closing of the mouth by the patient. A slot may be formed on the upper shell and/or the lower shell to receive one or more teeth of the patient for attaching the appliance to the mouth of the patient.

Referring now to the drawings wherein like numerals refer to like parts, FIG. 1 illustrates an appliance 1 in an open position for preventing snoring of a patient (not shown in the figures) in an embodiment of the present invention. The appliance 1 may be worn in the mouth of the patient and/or on a dentition of the patient for preventing snoring.

The dentition of the patient may include upper teeth, lower teeth, an upper jaw and/or a lower jaw. The upper teeth may be on the upper jaw and/or may extend outward and/or downward with respect to the upper jaw. The lower teeth may be on the lower jaw and/or may extend outward and/or upward with respect to the lower jaw. The teeth may have a cementoenamel junction at the intersection of crowns of the teeth with roots of the teeth.

The appliance 1 may have a lower shell 3 which may abut and/or may contact tops of the lower teeth of the patient. The lower shell 3 may be, for example, flat and/or indented to accommodate and/or to receive occlusal surfaces of the lower teeth. The appliance 1 may have an upper shell 2 which may abut and/or may contact tops of the upper teeth of the patient. The upper shell 2 may be, for example, flat and/or indented to accommodate and/or to receive occlusal surfaces of the upper teeth.

The lower shell 3 of the appliance 1 may have an anterior portion 11 and a posterior portion 1. The posterior portion 1 of the lower shell 3 may be in a position adjacent to the anterior portion 11 of the lower shell 3. The upper shell 2 of the appliance 1 may have an anterior portion 7 and a posterior portion 8. The posterior portion 8 of the upper shell 2 may be in a position adjacent to the anterior portion 7 of upper shell 2. The anterior portion 7 of the upper shell 2 of the appliance 1 may be adjacent to and/or may abut the anterior portion 11 of the lower shell 3 of the appliance 1. The posterior portion 8 of the upper shell 2 of the appliance 1 may be adjacent to and/or may abut the posterior portion 12 of the lower shell 3 of the appliance 1.

The appliance 1 may have a hinge 4 for connecting and/or attaching the lower shell 3 and the upper shell 2. The hinge 4 may connect to the posterior portion 8 of the upper shell 2 and/or to the posterior portion 12 of the lower shell 3. The hinge 4 may be connected and/or may be attached by integrally forming the hinge 4 with the appliance 1. Alternatively, the hinge 4 may be formed separately from the upper shell 2 and/or the lower shell 3 and subsequently attached to the upper shell 2 and/or the lower shell 3. The anterior portion 7 of the upper shell 2 may move inwardly and/or may move outwardly with respect to the anterior portion 11 of the lower shell 3. The upper shell 2 may rotate, may pivot and/or may move inwardly or outwardly with respect to the lower shell 3 via the hinge 4. The lower shell 3 of the appliance 1 may be integrally formed with the upper shell 2 such that the upper shell 2 and the lower shell 3 are formed from a single piece of material. Alternatively, the upper shell 2 and the lower shell 3 may be formed from different pieces of material and connected by the hinge 4.

In an embodiment as illustrated in FIG. 6, the appliance 1 may have the upper shell 2 and the lower shell 3 that may be detachable as discussed below. A removable hinge 24 may have a first end 25 that inserts into the upper shell 2 and/or a second end 26 that inserts into the lower shell 3. The removable hinge 24 may fold at a pivot 27 between the first end 25 and the second end 26, and the point 27 may be located at a position outside of the upper shell 2 and the lower shell 3. Thus, the removable hinge 24 may attach the upper shell 2 to the lower shell 3 and may be constructed from, for example, metal, plastic, rubber or other material. The removable hinge 24 may be secured by, for example, interlocking male and female fasteners (not shown), or other like method. The removable hinge 24 may be removed from the slots 21 in the upper shell 2 and/or the lower shell 3 to allow the upper shell 2 to separate in its entirety from the lower shell 3. The removable hinge 24 may re-insert into the slots 21 to re-attach the upper shell 2 to the lower shell 3.

The appliance 1 may be constructed from, for example, rubber, plastic, polyurethane, polyethylene, polypropylene and/or polyvinyl-chloride. Further, the appliance 1 may be constructed from, for example, a stiff polymer material, a soft polymer material, a combination of both a stiff polymer material and/or a soft polymer material. It should be understood that the appliance 1 may be constructed from any material as known to one having ordinary skill in the art.

The appliance 1 may be preformed or may be custom-made in the open position to be worn on the dentition of the patient. As a result, the appliance 1 may be sized to receive the dentition of the patient. The appliance 10 may be formed in a one-size-fits-all version which may be sized to be worn on the dentition of the patient. The appliance 1 may be formed in various sizes which may correspond to and/or may be based on dentitions of one or more patients. As a result, the appliance 10 may be worn on dentitions of various sizes by patients of various ages.

To improve retention of the appliance 1 within the mouth when the appliance 1 is worn in the mouth by the patient, a liner 20 may be incorporated within the upper slot 10 and/or the lower slot 13. The liner 20 may increase an ability of the appliance 1 to stay in the mouth, particularly while the patient is sleeping. The liner 20 may be constructed from, for example, hard or soft resilient plastic, rubber, a self-cure acrylic, a silicone or PVC-like denture lining material, or other like material that may be placed within the upper slot 10 and/or the lower slot 13. In a preferred embodiment, the liner 20 may be formed from a material that may be retained in the mouth of the patient.

As shown in FIG. 1, an upper margin 28 and/or a lower margin 29 may be formed on and/or may be attached to the anterior portion 7 of the upper shell 2 and/or the posterior portion 8 of the upper shell. A lower margin 29 may be formed on and/or may be attached to the anterior portion 11 of the lower shell 3 and/or the posterior portion 12 of the lower shell 3. The upper margin 28 and/or the lower margin 29 may be integrally formed with the appliance 1. The upper margin 28 may be located above and/or may be elevated above the cemento-enamel junction of the upper front incisors and/or posterior teeth of the patient when the appliance 1 may be worn in the mouth of the patient. The lower margin 29 may be located below and/or may descend below the cemento-enamel junction of the lower front incisors and/or posterior teeth of the patient when the appliance 1 may be worn in the mouth of the patient. The upper margin 28 and/or the lower margin 29 may be positioned between the upper front incisors and the upper lip of the patient and/or the lower front incisors and the lower lip of the patient, respectively. The upper margin 28 and/or the lower margin 29 may extend on a labial side, a buccal side and/or a buccal side of the mouth of the patient.

The upper margin 28 and/or the lower margin 29 may maintain the appliance 1 within the mouth of the patient such as when, for example, the patient may be sleeping. The upper margin 28 and/or the lower margin 29 may prevent the appliance 1 from moving rearward with respect to the mouth of the patient by abutting and/or by contacting the upper front incisors and/or the lower front incisors of the patient. As a result, the appliance 1 may be retained within the mouth of the patient by the upper margin 28 of the upper shell 2 and/or the lower margin 29 of the lower shell 3.

The anterior portion 7 of the upper shell 2 may separate from the anterior portion 11 of the lower shell 3 while the hinge 4 connects the posterior portion 8 of the upper shell 2 to the posterior portion 12 the lower shell 3. Separation of the upper shell 2 and the lower shell 3 via the hinge 4 may prevent the appliance 1 from being removed from the mouth of the patient when the mouth of the patient may be opened when the patient may be sleeping. As a result, the appliance 1 may be maintained and/or may be retained within the mouth of the patient via the hinge 4.

The appliance may maintain the lower jaw in a forward position relative to the mouth of the patient wherein the position provides an open airway to prevent snoring of the patient. Further, the appliance may maintain an open position of the mouth wherein the anterior portion of the upper jaw is positioned at a distance from the anterior portion of the lower jaw. The open position of the appliance 1 may hold the mouth of the patient in the open position to allow the patient to breathe through the mouth. As a result, the airway is open to prevent snoring of the patient.

The upper shell 2 and/or the lower shell 3 may be made from a first material. The hinge 4 may be made from a second material that is a different material than that of the first material. The second material may have a different grade of material stiffness, softness and/or resiliency. The first material may be formed from a material that may make the upper shell 2 and/or the lower shell 3 less prone to cutting into gum tissue and/or to causing irritation or sore spots. The second material of the hinge 4 may be formed from a material that may create resistance against and/or may prevent moving the appliance 1 from the open position to the closed position. The resistance against movement of the appliance 1 from the open position to the closed position may assist the patient in maintaining the upper jaw of the patient in an open position relative to the lower jaw of the patient. Therefore, the second material of the hinge 4 may maintain an open airway in the mouth of the patient to prevent snoring by creating resistance against closing the mouth. Additionally, the first material of a first appliance 1 may be used to allow the patient to become accustomed to wearing the appliance 1. Subsequently, another appliance 1 manufactured from a material harder than the first material may be provided to more forcefully position the lower jaw relative to the upper jaw.

As generally shown in FIGS. 1 and 6, the appliance 1 may have wedges 6 formed between the upper shell 2 and the lower shell 3. The wedges 6 may have an apex 100 at which nonparallel sides 101 of each of the wedges 6 meet. The wedges 6 may protrude in a direction forward in the mouth from the hinge 4, as shown in FIG. 1, or from the hinge 24, as shown in FIG. 6. Alternatively, the wedges 6 may be attached to the upper shell 2 and/or the lower shell 3. As generally shown in FIG. 6, in an embodiment of the upper shell 2 and the lower shell 3 as separate structures, the wedges 6 may be formed by a projecting portion of the upper shell 2 and/or the lower shell 3. The wedges 6 may be constructed from the same material as the upper shell 2 and/or the lower shell 3. In an embodiment in which the hinge 4 is made from the material stiffer than the material of the upper shell 2 and/or the material of the lower shell 3, the wedges 6 may be made from the stiffer material. For example, the wedges may be made of metal, hard or soft resilient plastic, rubber, a self-cure acrylic, a silicone or PVC-like material, rubber, plastic, polyurethane, polyethylene, polypropylene and/or polyvinyl-chloride. Furthermore, the wedges 6 may prevent the upper shell 2 and/or the lower shell 3 from shifting while being worn in the mouth of the patient.

As generally shown in FIGS. 4 and 5, lower jaw advancement by the appliance 1 may be customized based on a severity of the snoring of the patient and/or a position of the lower jaw relative to the upper jaw in the patient. The position of the lower shell 3 of the appliance 1 relative to the upper shell 2 of the appliance 1 may be based on the position of the lower jaw relative to the upper jaw in the patient. The appliance 1 may correct a forward position of the lower jaw in relation to the upper jaw by moving the lower teeth in a rearward position in relation to the upper teeth. A position of the lower jaw approximately three millimeters forward relative to the upper jaw is ideal to prevent snoring. For example, a mild snorer may have a position of the lower jaw three millimeters forward relative to the upper jaw; a moderate snorer may have a position of the lower jaw five millimeters forward relative to the upper jaw; and a severe snorer may have a position of the lower jaw eight millimeters forward relative to the upper jaw.

The severity of the snoring may indicate the adjustment to the position of the lower jaw relative to the upper jaw necessary to minimize and/or prevent snoring. Moreover, more than one appliance 1 may be used to treat the patient. Namely, a first appliance 1 may adjust the position of the lower jaw relative to the upper jaw to a first position forward in the mouth, and a second appliance 1 may adjust the position of the lower jaw relative to the upper jaw to a second position further forward in the mouth. The first appliance 1 may allow the patient to become accustomed to the appliance 1 so that the second appliance 1 may move the lower jaw further forward in the mouth relative to the upper jaw.

In an embodiment, the upper slot 10 may be formed in the upper shell 2 and/or the lower slot 13 may be formed in the lower shell 3 for wearing the appliance 1 on the dentition within the mouth of the patient. The upper slot 10 and/or the lower slot 13 may be custom-made to fit the upper teeth and/or the lower teeth of the patient, respectively, when the patient may be wearing the appliance 1. The upper slot 10 and/or the lower slot 13 may be adjacent to, may contact and/or may abut the tops of the upper teeth and/or the lower teeth of the patient, respectively, when the patient may be wearing the appliance 1. The lower teeth and/or the upper teeth of the patient may be inserted into the lower slot 13 and/or the upper slot 10, respectively, when the appliance 1 may be worn in the mouth by the patient.

The upper slot 10 and/or the lower slot 13 may provide one or more sockets 30, as generally shown in FIG. 6, to receive one or more of the upper teeth and/or the lower teeth of the patient to wear the appliance 1 within the mouth of the patient. The sockets 30 may surround one or more of the teeth of the patient by providing a labial wall, a buccal wall, a lingual wall, a mesial wall and/or a distal wall that may contact the teeth. Alternatively, the upper slot 10 and/or the lower slot 13 may be partitioned into two or more slots (not shown in the figures) to receive one or more of the upper teeth and/or of the lower teeth of the patient to wear the appliance 1 within the mouth of the patient. As a result, the upper slot 10 and/or the lower slot 13 may be shaped based on the dentition of the patient to match a size of the dentition and/or to provide a comfortable orthodontic appliance that may prevent snoring.

Referring now to FIG. 7, a front view is provided of a closed version of the appliance 1 in an embodiment of the present invention. The closed version may have the upper shell 2 formed integrally with the lower shell 3 so that the appliance 1 may be one piece. The closed version of the appliance 1 may create resistance against and/or may prevent moving the appliance 1 from the closed position to the open position. The resistance against movement of the appliance 1 from the closed position to the open position may assist the patient in maintaining the upper jaw of the patient in a closed position relative to the lower jaw of the patient. The closed version of the appliance 1 may maintain the lower jaw in the forward position relative to the mouth of the patient wherein the forward position provides an open airway to prevent snoring of the patient.

The appliance 1 may have breathing holes 104 that may be located in the anterior portion 11 of the lower shell 3 and/or the anterior portion 7 of the upper shell 2. The breathing holes 104 may extend from the labial side of the appliance 1 to a lingual side of the appliance 1. The breathing holes 104 may enable the patient to bite into the appliance 1 for an extended time while maintaining breathing. Further, the breathing holes 104 may enable the patient to maintain breathing if the appliance 1 is used in the closed position.

The upper margin 28 of the closed version of the appliance 1 may have may be formed on and/or may be attached to the anterior portion 7 of the upper shell 2. The upper margin 28 may be integrally formed with the appliance 1. The upper margin 28 may be located above and/or may be elevated above the cemento-enamel junction of the upper front incisors and/or posterior teeth of the patient when the appliance 1 may be worn in the mouth of the patient. The upper margin 28 may be positioned between the upper front incisors and the upper lip of the patient. The upper margin 28 and/or the lower margin 29 may extend on a labial side, a buccal side and/or a buccal side of the mouth of the patient.

Snoring may be caused by occlusion of an upper air passage during sleep. Therefore, oxygen may be applied to a nose and/or nostrils of the patient in combination with use of the appliance 1. Application of the oxygen and/or forced air to the nose and/or the nostrils of a patient may decrease and/or prevent the occlusion of the upper air passage. Further, because an amount of oxygen in blood of the patient may decrease due to snoring, the application of the oxygen and/or the forced air to the nose and/or the nostrils of the patient may prevent the decrease of the oxygen in the blood of the patient.

The application of the oxygen may allow the patient to maintain breathing if the appliance 1 is used in the closed position.

The appliance 1 may be designed by a computer. The computer (not shown) may generate a model or a digital three-dimensional (3-D) model of the teeth of the patient for creation of the dental appliance. The computer may generate the model using any digital source, such as, for example, laser scanned models of the teeth, digital photos and/or x-rays. Thus, to aid retention of the appliance 1 in the mouth of the patient, the appliance 1 may have some areas designed by the computer as a replication of a portion of the dentition of the patient. Alternatively, the appliance 1 may be designed by, for example, vacuum formation, pressure formation, stereolithography directly from a digital 3-D image of the mouth or by a like fabrication method.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. An apparatus for preventing snoring by a user wherein the user has a first plurality of teeth and a second plurality of teeth, the apparatus comprising:
    a first U-shaped base that has first walls that define a first interior adapted to receive the first plurality of teeth and further wherein the first U-shaped base has an anterior portion and a posterior portion;
    a second U-shaped base that has second walls that define a second interior wherein the second interior is adapted to receive the second plurality of teeth wherein the second U-shaped base has an anterior portion and a posterior portion and further wherein the anterior portion of the first U-shaped base is located at a distance from the anterior portion of the second U-shaped base wherein the anterior portion of the first U-shaped base does not contact the anterior portion of the second U-shaped base;
    a hinge that connects the posterior portion of the first U-shaped base to the posterior portion of the second U-shaped base; and
    wedges connected to the hinge wherein the wedges protrude from the hinge in a direction toward the anterior portion of the first U-shaped base and the anterior portion of the second U-shaped base and further wherein the wedges are located between the first U-shaped base and the second U-shaped base and prevent the anterior portion of the first U-shaped base from contacting the anterior portion of the second U-shaped base and maintain the distance of the anterior portion of the first U-shaped base from the anterior portion of the second U-shaped base.

2. The apparatus of claim 1 further comprising:
    an apex at which nonparallel sides of each of the wedges meet wherein each of the nonparallel sides faces an opposite direction.

3. The apparatus of claim 1 wherein the hinge extends from the first U-shaped base and the second U-shaped base in a first direction and further wherein the wedges extend from the first U-shaped base and the second U-shaped base in a second direction wherein the second direction is opposite to the first direction.

4. The apparatus of claim 1 further comprising:
an apex at which nonparallel sides of each of the wedges meet wherein one of the nonparallel sides faces the first U-shaped base and the other nonparallel side faces the second U-shaped base.

5. The dental appliance of claim 1 further comprising:
a slot in the first U-shaped base wherein the slot extends from the anterior portion to the posterior portion.

6. A system for preventing snoring by a user wherein the user has an upper jaw, a lower jaw, upper teeth and lower teeth, the system comprising:
a dental appliance having an upper shell and a lower shell wherein the upper shell has an upper interior adapted to receive the upper teeth and further wherein the upper shell has an anterior portion and a posterior portion wherein the lower shell has a lower interior adapted to receive the lower teeth and further wherein the lower shell has an anterior portion and a posterior portion and further wherein the anterior portion of the lower shell is located at a distance from the anterior portion of the upper shell;
a hinge that connects the posterior portion of the lower shell to the posterior portion of the upper shell; and
wedges connected to the hinge wherein the wedges are located between the upper shell and the lower shell and prevent the anterior portion of the lower shell from contacting the anterior portion of the upper shell and maintain the distance of the anterior portion of the lower shell from the anterior portion of the upper shell wherein the lower shell moves the lower jaw in a forward direction relative to the upper jaw.

7. The system of claim 6 further comprising:
an apex at which nonparallel sides of each of the wedges meet wherein one of the nonparallel sides faces the upper shell and further wherein the other nonparallel side faces the lower shell.

8. The system of claim 6 wherein the hinge is integrally formed with the dental appliance to connect the posterior portion of the upper shell to the posterior portion of the lower shell.

9. The dental appliance of claim 6 further comprising:
a slot in the dental appliance wherein the slot extends between the anterior portion and the posterior portion.

10. A method for preventing snoring of a patient wherein the patient has a mouth, an airway, an upper jaw, a lower jaw connected to the upper jaw, upper teeth connected to the upper jaw and lower teeth connected to the lower jaw, the method comprising the step of:
positioning a dental appliance in the mouth of the patient wherein the dental appliance has an upper U-shaped base, a lower U-shaped base and a hinge and further wherein the dental appliance has wedges which protrude from the hinge in a direction forward in the mouth wherein the hinge connects the upper U-shaped base to the lower U-shaped base wherein the upper U-shaped base receives the upper teeth and the lower U-shaped base receives the lower teeth and further wherein the dental appliance moves the lower jaw in a forward direction relative to the mouth and further wherein moving the lower jaw in the forward direction relative to the mouth opens the airway of the patient.

11. The method of claim 10 further comprising the step of:
preventing movement of the upper U-shaped base in a direction toward the lower U-shaped base wherein each of the wedges has an apex at which nonparallel sides meet and further wherein the upper U-shaped base and the lower U-shaped base contacting the nonparallel sides prevents movement of the upper U-shaped base in a direction toward the lower U-shaped base to prevent the patient from closing the mouth.

12. The method of claim 10 wherein the hinge extends from the dental appliance in a first direction and further wherein the wedges extend in a second direction wherein the second direction is opposite to the first direction.

13. The method of claim 10 wherein the dental appliance has a slot in at least one of the upper U-shaped base and the lower U-shaped base.

14. A method for preventing snoring of a patient wherein the patient has nostrils, a mouth, an airway, an upper jaw, a lower jaw connected to the upper jaw, upper teeth connected to the upper jaw and lower teeth connected to the lower jaw, the method comprising the step of:
positioning a dental appliance in the mouth of the patient wherein the dental appliance has an upper U-shaped base and a lower U-shaped base and further wherein the dental appliance has a posterior portion and an anterior portion wherein the anterior portion is located in a position opposite to the posterior portion and further wherein the upper U-shaped base is connected to the lower U-shaped base at the posterior portion of the dental appliance wherein the upper U-shaped base receives the upper teeth and the lower U-shaped base receives the lower teeth and further wherein the dental appliance moves the lower jaw in a forward direction relative to the mouth and further wherein moving the lower jaw in the forward direction relative to the mouth opens the airway of the patient wherein the dental appliance has wedges which protrude from the posterior portion of the dental appliance in a direction toward the anterior portion of the dental appliance; and
customizing the dental appliance to fit the upper teeth and the lower teeth of the patient.

15. The method of claim 14 further comprising the step of:
applying oxygen to the nostrils of the user.

16. A method for preventing snoring of a patient wherein the patient has a mouth, an airway, an upper jaw, a lower jaw connected to the upper jaw, upper teeth connected to the upper jaw and lower teeth connected to the lower jaw, the method comprising the step of:
positioning a dental appliance in the mouth of the patient wherein the dental appliance has an upper U-shaped base and a lower U-shaped base wherein the upper U-shaped base receives the upper teeth and the lower U-shaped base receives the lower teeth and further wherein the dental appliance moves the lower jaw in a forward direction relative to the mouth and further wherein moving the lower jaw in the forward direction relative to the mouth opens the airway of the patient wherein the dental appliance has wedges that extend in the forward direction relative to the mouth; and
customizing the dental appliance wherein the dental appliance is customized to hold the upper jaw and the lower jaw in a closed position when the lower jaw is moved in the forward direction relative to the mouth.

17. The method of claim 16 further comprising the step of:
applying oxygen to the nostrils of the user.

18. A method for preventing snoring of a patient wherein the patient has a mouth, an airway, an upper jaw, a lower jaw connected to the upper jaw, upper teeth connected to the upper jaw and lower teeth connected to the lower jaw, the method comprising the step of:
determining a severity of the snoring wherein the severity of snoring is based on a position of the lower jaw relative to the upper jaw;

positioning a dental appliance in the mouth of the patient wherein the dental appliance has an upper U-shaped base, a lower U-shaped base and a hinge wherein the hinge connects the upper U-shaped base to the lower U-shaped base wherein the upper U-shaped base receives the upper teeth and the lower U-shaped base receives the lower teeth and further wherein the dental appliance moves the lower jaw in a forward direction relative to the mouth and further wherein moving the lower jaw in the forward direction relative to the mouth opens the airway of the patient; and customizing the dental appliance wherein the dental appliance is customized to hold the upper jaw and the lower jaw in an open position when the lower jaw is moved in the forward direction relative to the mouth and further wherein the lower jaw is moved a distance in the forward direction wherein the distance is based on the severity of the snoring.

19. The method of claim 18 further comprising the step of:

applying oxygen to the nostrils of the user.

20. An apparatus for preventing snoring by a user wherein the user has a first plurality of teeth, a second plurality of teeth, a lower jaw and an upper jaw, the apparatus comprising:

a first U-shaped base that has first walls that define a first interior adapted to receive the first plurality of teeth and further wherein the first U-shaped base has an anterior portion and a posterior portion wherein the anterior portion of the first U-shaped base extends to a first point and further wherein the first point is located above the first plurality of teeth;

a second U-shaped base that has second walls that define a second interior wherein the second interior is adapted to receive the second plurality of teeth wherein the second U-shaped base has an anterior portion and a posterior portion wherein the anterior portion of the second U-shaped base extends to a second point and further wherein the second point is located below the second plurality of teeth and further wherein the anterior portion of the first U-shaped base is located at a distance from the anterior portion of the second U-shaped base wherein the second U-shaped base moves the lower jaw in a forward direction relative to the upper jaw wherein the first U-shaped base and the second U-shaped base maintain the distance between the anterior portion of the first U-shaped base and the anterior portion of the second U-shaped base and prevents movement of the first U-shaped base in a direction away from the second U-shaped base wherein preventing movement of the first U-shaped base in a direction away from the second U-shaped base prevents the patient from opening the mouth;

a hinge which connects the posterior portion of the first U-shaped base to the posterior portion of the second U-shaped base; and wedges which protrude from the hinge toward the anterior portion of the first U-shaped base and the anterior portion of the second U-shaped base.

21. A method for preventing snoring of a patient wherein the patient has a mouth, an airway, an upper jaw, a lower jaw connected to the upper jaw, upper teeth connected to the upper jaw and lower teeth connected to the lower jaw, the method comprising the step of:

obtaining an image of the upper jaw, the lower jaw, the upper teeth and the lower teeth wherein the image indicates a position of the lower jaw relative to the upper jaw;

determining a severity of the snoring of the patient wherein the severity of the snoring is based on the position of the lower jaw relative to the upper jaw indicated by the image;

designing a dental appliance having an upper U-shaped base and a lower U-shaped base wherein the dental appliance is designed by a computer and further wherein the dental appliance is designed to move the lower jaw a distance in a forward direction relative to the upper jaw wherein the distance is based on the severity of snoring of the patient; and forming the dental appliance wherein the upper U-shaped base receives the upper teeth and the lower U-shaped base receives the lower teeth and further wherein the dental appliance moves the lower jaw the distance in the forward direction relative to the upper jaw and further wherein moving the lower jaw the distance in the forward direction relative to the mouth opens the airway of the patient.

22. An apparatus for preventing snoring by a user wherein the user has nostrils, a first plurality of teeth, a second plurality of teeth, a lower jaw and an upper jaw, the apparatus comprising:

a first U-shaped base that has first walls that define a first interior adapted to receive the first plurality of teeth and further wherein the first U-shaped base has an anterior portion and a posterior portion wherein the anterior portion of the first U-shaped base extends to a first point and further wherein the first point is located above the first plurality of teeth;

a second U-shaped base that has second walls that define a second interior wherein the second interior is adapted to receive the second plurality of teeth wherein the second U-shaped base has an anterior portion and a posterior portion wherein the anterior portion of the second U-shaped base extends to a second point and further wherein the second point is located below the second plurality of teeth and further wherein the anterior portion of the first U-shaped base is located at a distance from the anterior portion of the second U-shaped base wherein the second U-shaped base moves the lower jaw in a forward direction relative to the upper jaw wherein the first U-shaped base and the second U-shaped base maintain the distance between the anterior portion of the first U-shaped base and the anterior portion of the second U-shaped base and prevents movement of the first U-shaped base in a direction away from the second U-shaped base wherein preventing movement of the first U-shaped base in a direction away from the second U-shaped base prevents the patient from opening the mouth;

wedges that extend from at least one of the posterior portion of the first U-shaped base and the posterior portion of the second U-shaped base wherein the wedges extend in the forward direction; and means for applying oxygen to the nostrils of the user.

23. A method for preventing snoring of a patient wherein the patient has nostrils, a mouth, an airway, an upper jaw, a lower jaw connected to the upper jaw, upper teeth connected to the upper jaw and lower teeth connected to the lower jaw, the method comprising the step of:

positioning a dental appliance in the mouth of the patient wherein the dental appliance has an upper U-shaped base and a lower U-shaped base and further wherein the dental appliance has a posterior portion and an anterior portion wherein the anterior portion is located in a position opposite to the posterior portion and further wherein the upper U-shaped base is connected to the lower U-shaped base at the posterior portion of the dental appliance wherein the upper U-shaped base receives the upper teeth and the lower U-shaped base receives the lower teeth and further wherein the dental appliance moves the lower jaw in a forward direction relative to the mouth and further wherein moving the lower jaw in the forward direction relative to the mouth opens the airway of the patient wherein the dental appliance has wedges which protrude from the posterior portion of the dental appliance in a direction toward the anterior portion of the dental appliance; and customizing one of the upper U-shaped base and the lower U-shaped base to fit one of the upper teeth and the lower teeth of the patient.

24. A method for preventing snoring of a patient wherein the patient has a mouth, an airway, an upper jaw, a lower jaw connected to the upper jaw, upper teeth connected to the upper jaw and lower teeth connected to the lower jaw, the method comprising the step of:

positioning a dental appliance in the mouth of the patient wherein the dental appliance has an upper U-shaped base and a lower U-shaped base wherein the upper U-shaped base receives the upper teeth and the lower U-shaped base receives the lower teeth and further wherein the dental appliance moves the lower jaw in a forward direction relative to the mouth and further wherein moving the lower jaw in the forward direction relative to the mouth opens the airway of the patient wherein the dental appliance has wedges that extend in the forward direction relative to the mouth; and customizing at least one of the upper U-shaped base and the lower U-shaped base to hold the upper jaw and the lower jaw in a closed position when the lower jaw is moved in the forward direction relative to the mouth.

25. A method for preventing snoring of a patient wherein the patient has a mouth, an airway, an upper jaw, a lower jaw connected to the upper jaw, upper teeth connected to the upper jaw and lower teeth connected to the lower jaw, the method comprising the step of:

determining a severity of the snoring wherein the severity of snoring is based on a position of the lower jaw relative to the upper jaw;

positioning a dental appliance in the mouth of the patient wherein the dental appliance has an upper U-shaped base, a lower U-shaped base and a hinge wherein the hinge connects the upper U-shaped base to the lower U-shaped base wherein the upper U-shaped base receives the upper teeth and the lower U-shaped base receives the lower teeth and further wherein the dental appliance moves the lower jaw in a forward direction relative to the mouth and further wherein moving the lower jaw in the forward direction relative to the mouth opens the airway of the patient; and customizing at least one of the upper U-shaped base and the lower U-shaped base to hold the upper jaw and the lower jaw in an open position when the lower jaw is moved in the forward direction relative to the mouth and further wherein the lower jaw is moved a distance in the forward direction wherein the distance is based on the severity of the snoring.

* * * * *